US012788943B2

(12) United States Patent
Koiso et al.

(10) Patent No.: US 12,788,943 B2
(45) Date of Patent: Nov. 10, 2026

(54) DRUG SOLUTION INJECTION NEEDLE AND DRUG SOLUTION INJECTION NEEDLE SYSTEM

(71) Applicant: JAPAN LIFELINE CO., LTD., Tokyo (JP)

(72) Inventors: Tomoharu Koiso, Tokyo (JP); Aki Hoshida, Tokyo (JP); Masaki Yoshinuma, Tokyo (JP); Kenji Mori, Tokyo (JP); Takeshi Machino, Tsukuba (JP); Akira Sato, Tsukuba (JP); Nobuyuki Murakoshi, Tsukuba (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 904 days.

(21) Appl. No.: 17/908,736

(22) PCT Filed: Mar. 27, 2020

(86) PCT No.: PCT/JP2020/014251
§ 371 (c)(1),
(2) Date: Sep. 1, 2022

(87) PCT Pub. No.: WO2021/192283
PCT Pub. Date: Sep. 30, 2021

(65) Prior Publication Data

US 2023/0118399 A1 Apr. 20, 2023

(51) Int. Cl.

*A61M 25/00* (2006.01)
*A61B 17/34* (2006.01)
*A61M 5/172* (2006.01)

(52) U.S. Cl.

CPC ....... *A61M 25/007* (2013.01); *A61B 17/3478* (2013.01); *A61M 25/0084* (2013.01); *A61M 2005/1726* (2013.01)

(58) Field of Classification Search

CPC ............ A61M 25/0084; A61M 25/007; A61M 2005/1726; A61M 5/158; A61M 2205/13;
(Continued)

(56) References Cited

U.S. PATENT DOCUMENTS 6,241,710 B1 6/2001 Vantassel et al.
2004/0193152 A1 * 9/2004 Sutton .................... A61B 18/18 606/50
(Continued)

FOREIGN PATENT DOCUMENTS

CN 101536902 A 9/2009
CN 110769888 A 2/2020
(Continued)

OTHER PUBLICATIONS

Office Action dated Sep. 22, 2023 issued in corresponding Chinese Patent Application No. 202080099038.2 (with English translation), 12 pages.
(Continued)

*Primary Examiner* — James D Ponton
(74) *Attorney, Agent, or Firm* — Shih IP Law Group, PLLC

(57) ABSTRACT

A drug solution injection needle includes: a distal end member being a sharp member and made of metal; a connecting tube having electrical insulating properties connected to a base end side of the distal end member; a metal tube connected to a base end side of the connecting tube; and an insulating layer covering an outer circumferential surface of a base end portion of the metal tube. The connecting tube and/or the distal end member includes at least one hole communicating with a cavity of the drug solution injection needle and open to an outer surface of the connecting tube or the distal end member, and an electrode configured to
(Continued)

measure electric potential is formed by a distal end portion of the metal tube not covered by the insulating layer.

7 Claims, 8 Drawing Sheets

(58) Field of Classification Search
CPC ........ A61M 2210/125; A61M 25/0158; A61M 25/0082; A61B 17/3478; A61B 2018/1467
See application file for complete search history.

(56) References Cited

U.S. PATENT DOCUMENTS

| | | | | |
|---|---|---|---|---|
| 2005/0165354 | A1 | 7/2005 | Schwartz et al. | |
| 2009/0088695 | A1* | 4/2009 | Kapur | A61M 25/0054 604/164.01 |
| 2009/0171304 | A1 | 7/2009 | Cao et al. | |
| 2018/0296263 | A1 | 10/2018 | Mori | |
| 2020/0139086 | A1* | 5/2020 | Serra De Mattos | A61B 5/15003 |
| 2020/0170670 | A1* | 6/2020 | Sasazawa | A61M 25/06 |

FOREIGN PATENT DOCUMENTS

| | | | |
|---|---|---|---|
| DE | 202013010300 | U1 | 2/2015 |
| JP | 2003517863 | A | 6/2003 |
| JP | 2004-267532 | A | 9/2004 |
| JP | 2004290582 | A | 10/2004 |
| JP | 4249514 | B2 | 4/2009 |
| JP | 2011507648 | A | 3/2011 |
| JP | 2018000400 | A | 1/2018 |
| WO | WO9949926 | | 10/1999 |
| WO | WO2018219842 | A1 | 12/2018 |
| WO | WO2019049628 | A1 | 3/2019 |

OTHER PUBLICATIONS

An Office Action in corresponding JP Application No. 2022-510382 dated May 9, 2023 is attached, 2 pages.
Australian Office Action for Application No. 2020437982, Sep. 18, 2023.
An Office Action dated Mar. 10, 2025 issued in corresponding Singapore Patent Application No. 11202252332P, 9 pages.
Office Action mailed Apr. 17, 2024 in Canada Application 3168430, 5 pages.

* cited by examiner

DRUG SOLUTION INJECTION NEEDLE AND DRUG SOLUTION INJECTION NEEDLE SYSTEM

CROSS-REFERENCE TO RELATED APPLICATIONS

This application is based upon and claims the benefit of priority from the International Patent Application No. PCT/JP2020/014251, filed on Mar. 27, 2020, the entire content of each of which is incorporated herein by reference.

BACKGROUND

Field of the Invention

The present invention relates to a drug solution injection needle for puncturing the myocardium of a patient and injecting a drug solution and a drug solution injection needle system provided with the drug solution injection needle.

Description of the Related Art

In a known treatment method for regenerating cardiomyocytes, a drug solution such as a cardiac regenerative cell formulation is directly administered to cardiomyocytes losing their function due to a myocardial infarction or the like.

Note that diagnosis (mapping) with electrophysiology (EP) catheters or the like is performed to identify the target sites that require drug administration treatment prior to treatment.

To directly administer the drug solution to the cardiomyocytes, a hollow needle (drug solution injection needle) that punctures the myocardium of the patient and injects the drug solution is used (see Patent Document 1 below).

The drug solution injection needle is inserted into a sheath or guiding catheter and in this state is entered into a cavity (cardiac cavity) of a living body. When the distal end of the sheath or guiding catheter reaches at or near the target site, a needle tip of the drug solution injection needle is extended out from the leading end opening to puncture the target site (myocardium) and administer the drug solution to the cardiomyocytes.

Patent Document 1: WO 99/49926

However, in the case of drug administration treatment using a drug solution injection needle, it is important that the drug solution is reliably administered to the cardiomyocytes of the patient. Thus, when the drug solution is injected, the opening for drug solution injection in the needle tip of the drug solution injection needle needs to be located in the myocardium.

However, it is not easy to check whether the opening of the drug solution injection needle is located in the myocardium.

For example, as in the case of the drug solution injection needle described in Patent Document 1, even when cine imaging is used to check the position of a needle tip provided with a radiopaque band or the like, because the shape of the pulsating heart wall cannot be confirmed from the cine imaging, it is difficult to discern whether the needle tip is located inside the heart wall (myocardium) or located outside the heart wall (cardiac cavity).

SUMMARY OF THE INVENTION

The present invention has been made on the basis of the above-described circumstances.

The object of the present invention is to provide a drug solution injection needle that enables easy determination of whether an opening for drug solution injection is located inside a heart wall (myocardium) and that enables a drug solution to be reliably injected into the myocardium.

Another object of the present invention is to provide a drug solution injection needle system that enables a drug solution to be reliably injected into the myocardium.

A drug solution injection needle according to the present invention is a hollow needle for puncturing a myocardium of a patient and injecting a drug solution that includes a distal end member, the distal end member being a sharp member and made of metal; a connecting tube having electrical insulating properties connected to a base end side of the distal end member; a metal tube connected to a base end side of the connecting tube; and an insulating layer covering an outer circumferential surface of a base end portion of the metal tube, wherein the connecting tube and/or the distal end member includes at least one hole (outflow path for the drug solution) communicating with a cavity of the drug solution injection needle and open to an outer surface of the connecting tube or the distal end member; and an electrode configured to measure electric potential is formed by a distal end portion of the metal tube not covered by the insulating layer.

A drug solution injection needle system according to the present invention includes the drug solution injection needle according to the present invention and a notification unit configured to notify an operator that injection of the drug solution is possible when an electric potential measured by the electrode of the drug solution injection needle is equal to or greater than a predetermined value.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1:
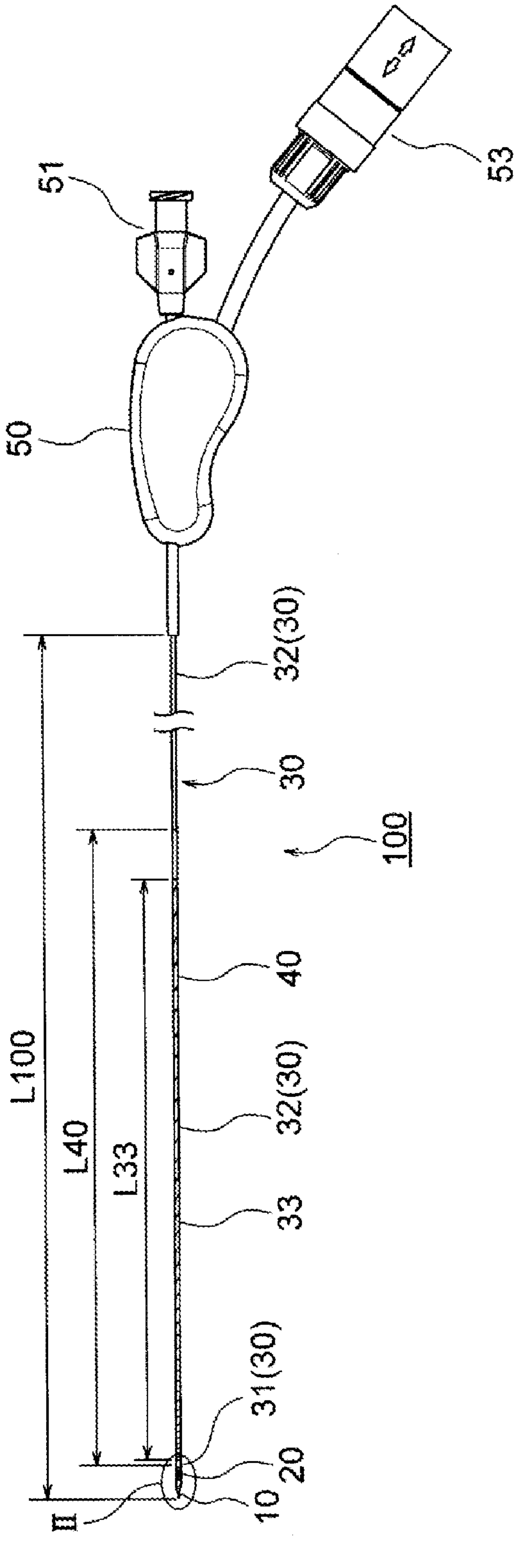
FIG. 1 is a front view illustrating a drug solution injection needle according to an embodiment of the present invention.

The invention will now be described by reference to the preferred embodiments. This does not intend to limit the scope of the present invention, but to exemplify the invention.

(1) A drug solution injection needle according to the present invention is a hollow needle for puncturing a myocardium of a patient and injecting a drug solution that includes a distal end member, the distal end member being a sharp member and made of metal; a connecting tube having electrical insulating properties connected to a base end side of the distal end member; a metal tube connected to a base end side of the connecting tube; and an insulating layer covering an outer circumferential surface of a base end portion of the metal tube, wherein the connecting tube and/or the distal end member includes at least one hole (outflow path for the drug solution) communicating with a cavity of the drug solution injection needle and open to an outer surface of the connecting tube or the distal end member; and an electrode configured to measure electric potential is formed by a distal end portion of the metal tube not covered by the insulating layer.

According to the drug solution injection needle with such a configuration, when the electrode constituted by the distal end portion of the metal tube is entered inside the heart wall (myocardium), the electric potential measured by the electrode rapidly increases (an electric potential of equal to or greater than a certain value can be acquired). Thus, by detecting a rapid increase in the electric potential, it can be confirmed that the electrode has been entered inside the heart wall.

The electrode (distal end portion of the metal tube) is located on the base end side of the hole formed in the connecting tube and/or the distal end member. Thus, when the electrode is located inside the heart wall, the opening (opening for drug solution injection) of the hole is also located inside the heart wall (myocardium).

Accordingly, by checking whether the electric potential measured by the electrode is equal to or greater than the predetermined value, whether the opening for drug solution injection is located inside the heart wall can be easily determined, and by injecting the drug solution after confirming that the electric potential is equal to or greater than the predetermined value, the drug solution can be reliably injected from the opening of the hole to the myocardium.

Also, because the metal tube and the insulating layer covering the outer circumferential surface of the base end portion are provided, the distal end portion of the metal tube can be used as an electrode and the base end portion of the metal tube can be used as the lead of the electrode.

This removes the need for separately providing a ring-shaped electrode on the outer surface of the needle or providing a lead line of the electrode inside or outside the metal tube. This allows the diameter of the needle to be reduced and allows sufficient cavity space of the needle to be ensured.

Furthermore, the metal distal end member constituting the drug solution injection needle and the metal tube are electrically insulated from one another via the connecting tube, and the distal end member does not form an electrode. Thus, the electric potential does not increase at the stage when the distal end member and the connecting tube are entered inside the heart wall, and the distal end portion (electrode) of the metal tube is not entered.

(2) In the drug solution injection needle according to the present invention, preferably, a distal end of the distal end member is closed, and a tube wall of the connecting tube includes a plurality of side holes communicating with the cavity of the needle (cavity of the connecting tube) and open to the outer circumferential surface of the connecting tube.

According to the drug solution injection needle with such a configuration, compared to a drug solution injection needle with a side hole formed in the distal end member, the length of the distal end portion of the needle with poor flexibility can be reduced.

(3) In the drug solution injection needle according to (2), preferably, side hole groups including the plurality of side holes arranged in an axial direction of the connecting tube are disposed at even angular intervals apart in a circumferential direction of the connecting tube.

According to a drug solution injection needle with such a configuration, the drug solution can be injected evenly in the axial direction (direction of the wall thickness of the myocardium) of the connecting tube and the circumferential direction of the connecting tube.

(4) In the drug solution injection needle according to (3), preferably, the side holes of the side hole groups located on a distal end side have a larger diameter than the side holes located on the base end side.

According to a drug solution injection needle with such a configuration, the drug solution can be injected further evenly in the axial direction of the connecting tube (direction of the wall thickness of the myocardium).

(5) In the drug solution injection needle according to the present invention, preferably, a helical slit is formed in a distal end region of the base end portion of the metal tube.

According to a drug solution injection needle with such a configuration, the stiffness of the distal end region of the base end portion of the metal tube is somewhat reduced by the helical slit, giving the injection needle flexibility.

(6) In the drug solution injection needle according to the present invention, preferably, the drug solution is a cardiac regenerative cell formulation.

(7) A drug solution injection needle system according to the present invention includes the drug solution injection needle according to the present invention and a notification unit configured to notify an operator that injection of the drug solution is possible when an electric potential measured by the electrode of the drug solution injection needle is equal to or greater than a predetermined value.

Drug Solution Injection Needle

Figure 2:
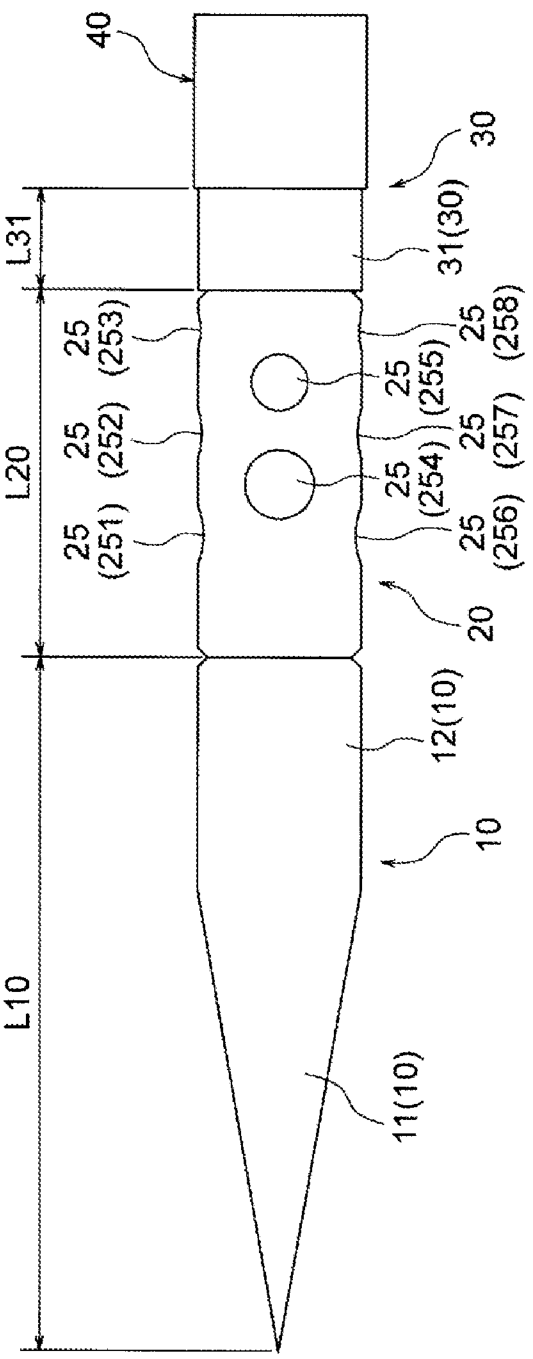
FIG. 2 is a partially enlarged front view (detailed view of portion II in FIG. 1) illustrating a distal end portion of the drug solution injection needle illustrated in FIG. 1.
Figure 3:
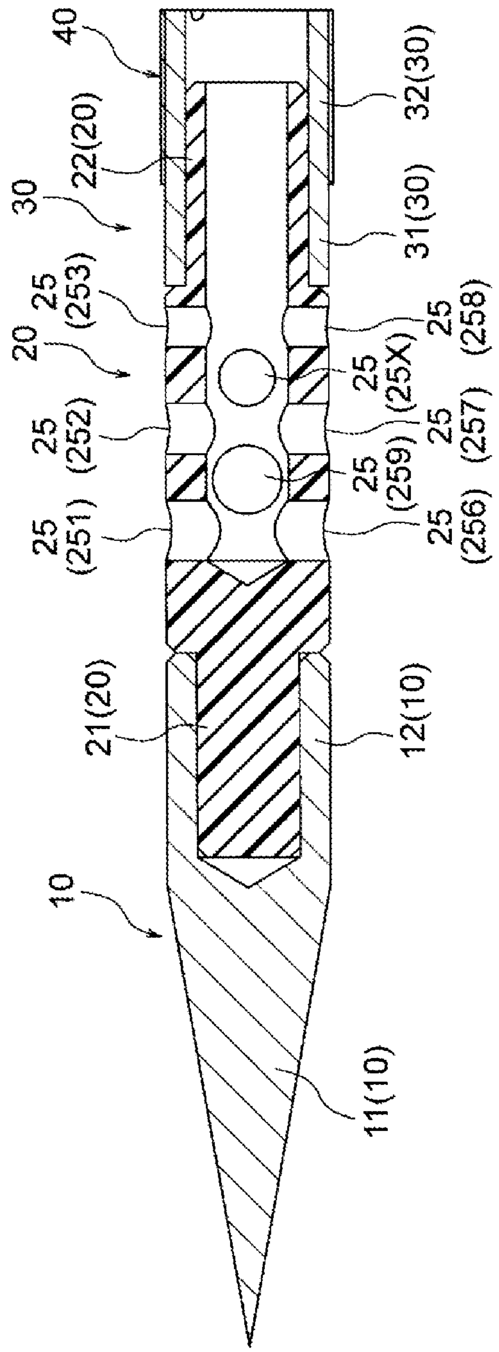
FIG. 3 is a partially enlarged cross-sectional view illustrating the distal end portion of the drug solution injection needle illustrated in FIG. 1.

A drug solution injection needle 100 of the embodiment illustrated in FIGS. 1 to 3 is a hollow needle for puncturing the myocardium of a patient and injecting a drug solution. The drug solution injection needle 100 includes a sharp distal end member 10 made of metal with a closed distal end, a connecting tube 20 having electrical insulating properties connected to the base end side of the distal end member 10, a metal tube 30 connected to the base end side of the connecting tube 20, and an insulating layer 40 covering the outer circumferential surface of a base end portion 32 of the metal tube 30. The connecting tube 20 is provided with ten side holes 25 (251 to 259, 25X) communicating with the cavity of the drug solution injection needle 100 and open to the outer circumferential surface of the connecting tube 20, and an electrode for measuring electric potential is formed by a distal end portion 31 of the metal tube 30 not covered by the insulating layer 40.

The drug solution injection needle 100 of the present embodiment is provided with the metal distal end member 10, the connecting tube 20 having electrical insulating properties, the metal tube 30, and the insulating layer 40.

As illustrated in FIG. 1, a gripping portion 50 is installed on the base end side of the metal tube 30 constituting the drug solution injection needle 100, and the drug solution injection needle 100 and the gripping portion 50 form a drug solution injection needle device.

The gripping portion 50 constituting the drug solution injection needle device is made of a resin, a rubber, an elastomer, or the like.

The gripping portion 50 is provided with an injection port 51 for supplying a drug solution to the cavity of the drug solution injection needle 100 and a connector 53 electrically connected with the electrode of the drug solution injection needle 100 via a lead welded to the base end of the metal tube 30.

The effective length (L100 illustrated in FIG. 1) of the drug solution injection needle 100 projecting from the distal end of the gripping portion 50 typically ranges from 800 to 2500 mm and in a preferable example is 1300 mm.

The outer diameter of the drug solution injection needle 100 typically ranges from 0.3 to 1.5 mm and in a preferable example is 0.8 mm.

The inner diameter of the drug solution injection needle 100 typically ranges from 0.1 to 1.3 mm and in a preferable example is 0.6 mm.

The drug solution injection needle 100 of the present embodiment is a hollow needle for puncturing the myocardium of a patient and injecting a drug solution to the cardiomyocytes.

Here, the term "drug solution" can include cell formulations such as a cardiac regenerative cell formulation and gene transfer agents.

As illustrated in FIG. 3, the distal end member 10 constituting the drug solution injection needle 100 is a metal member including a solid sharp portion 11 and a tubular portion 12 with internal space, and the distal end of the distal end member 10 is closed.

The length (L10 illustrated in FIG. 2) of the distal end member 10 typically ranges from 0.5 to 5 mm and in a preferable example is 2.5 mm.

If the length of the distal end member 10 is too short, the puncture performance may be impaired, or the joining strength with the connecting tube 20 may be decreased.

On the other hand, if the length of the distal end member 10 is too long, the ability of the drug solution injection needle 100 to follow a blood vessel may be impaired and entering the connecting tube 20 connected to the base end side of the distal end member 10 and the distal end portion 31 (electrode) of the metal tube 30 into the myocardium may be difficult.

Any known metal used in drug solution injection needles can be used as the metal constituting the distal end member 10, with examples including stainless steel, NiTi, β titanium, and platinum iridium.

Additionally, a portion or all of the distal end member 10 may be constituted by a radiopaque metal. This allows the position of the distal end member 10 up to the target site to be checked via cine imaging. Examples of a radiopaque metal include platinum and its alloys, gold, tungsten, and tantalum.

The connecting tube 20 constituting the drug solution injection needle 100 is made of a material having electrical insulating properties and is a member that connects the distal end member 10 and the metal tube 30 while ensuring the electrical insulating properties of both.

In some embodiments, the distal end member 10 and the metal tube 30 are connected via the connecting tube 20, but no such limitation is intended. As illustrated in FIG. 3, in the present embodiment, a distal end small diameter portion 21 of the connecting tube 20 is inserted into the internal space of the distal end member 10 (tubular portion 12), and a base end small diameter portion 22 of the connecting tube 20 is inserted into the leading end opening of the metal tube 30. The distal end member 10 and the metal tube 30 are connected in this manner.

As illustrated in FIG. 3, the cavity of the connecting tube 20 and the cavity of the metal tube 30 communicate with one another, forming the cavity of the drug solution injection needle 100.

The length (L20 illustrated in FIG. 2) of the connecting tube 20 typically ranges from 0.1 to 25 mm and in a preferable example is 14 mm.

If the length of the connecting tube 20 is too short, the distal end member 10 and the metal tube 30 may not be sufficiently insulated.

On the other hand, if the length of the connecting tube 20 is too long, the ability of the distal end portion of the drug solution injection needle 100 to follow a blood vessel may be impaired.

The electrically insulating material constituting the connecting tube 20 is not particularly limited, but preferably a resin material or a ceramic material is used. Using a resin material is particularly preferable because of its good electrical insulating properties and heat insulating properties and ease of forming.

The resin constituting the connecting tube 20 may be a thermoplastic resin or a thermosetting resin. Also, resin includes in its meaning ebonite. Specific examples include cyclic olefin-based resin, polyphenylene sulfide, polyether ether ketone (PEEK), polybutylene terephthalate, poly carbonate, polyamide, polyacetal, modified polyphenylene ether, polyester-based resin, polytetrafluoroethylene, fluororesin, sulfone-based resin, polyetherimide, poly ethersulfone, polyetherketone, polyether lactone, liquid crystal polyester, polyamideimide, polyimide, polyether nitrile, polypropylene, polyethylene, epoxy resin, unsaturated polyester resin, phenol resin, urea resin, melamine resin, and polyurethane resin. Of these, polyether ether ketone, polycarbonate, polyphenylsulfone, polyamide, and polyacetal are preferable.

In the connecting tube 20, as outflow paths for the drug solution to be injected, the ten side holes 25 (251 to 259, 25X) communicating with the cavity of the connecting tube 20 (drug solution injection needle 100) and open to the outer circumferential surface of the connecting tube 20 are formed.

As illustrated in FIGS. 2 and 3, a first side hole group including the side holes 251, 252, and 253, a second side hole group including side holes 254 and 255, a third side hole group including side holes 256, 257, and 258, and a fourth side hole group including side holes 259 and 25X are disposed at even angular intervals (90°) apart in the circumferential direction of the connecting tube 20.

Accordingly, the drug solution can be injected evenly in the axial direction (direction of the wall thickness of the myocardium) of the connecting tube 20 and the circumferential direction of the connecting tube 20.

Regarding the diameters of the side holes in the first side hole group, the side hole 251 located on the distal end side has the largest diameter, the side hole 252 located next in the middle region has a large diameter, and the side hole 253 located on the base end side has the smallest diameter.

Regarding the diameters of the side holes in the second side hole group, the side hole 254 located on the distal end side has a larger diameter than the side hole 255 located on the base end side.

Regarding the diameters of the side holes in the third side hole group, the side hole 256 located on the distal end side has the largest diameter, the side hole 257 located next in the middle region has a large diameter, and the side hole 258 located on the base end side has the smallest diameter.

Regarding the diameters of the side holes in the fourth side hole group, the side hole 259 located on the distal end side has a larger diameter than the side hole 25X located on the base end side.

As described above, by making the diameter of the side holes located on the distal end side larger than the diameter of the side holes located on the base end side, the discharge amount of the drug solution from the side holes in the same side hole group can be made even, and the drug solution can also be evenly injected in the axial direction (direction of the wall thickness of the myocardium) of the connecting tube 20.

For example, regarding to diameters of the side holes 25 (251 to 259, 25X), the diameter of the side hole 251 and the side hole 256 is 0.27 mm, the diameter of the side hole 252 and the side hole 257 is 0.23 mm, the diameter of the side hole 253 and the side hole 258 is 0.20 mm, the diameter of the side hole 254 and the side hole 259 is 0.30 mm, and the diameter of the side hole 255 and the side hole 25X is 0.25 mm.

The metal tube 30 constituting the drug solution injection needle 100 is made of a tubular member provided with a cavity that communicates with the cavity of the connecting tube 20.

The length (L100-L10-L20) of the metal tube 30 typically ranges from 800 to 2500 mm and in a preferable example is 1283.5 mm.

The metal tube 30 requires the stiffness (particularly bending stiffness) and elasticity (particularly bending elasticity) required for a typical drug solution injection needle.

The metal constituting the metal tube 30 can be the same metal as that used for the distal end member 10, for example. Additionally, a portion or all of the distal end portion 31 of the metal tube 30 may be constituted by a radiopaque metal. This allows the position of the electrode up to the target site to be checked via cine imaging.

As illustrated in FIG. 1, a helical slit 33 is formed in the distal end region of the base end portion 32 of the metal tube 30. Accordingly, the stiffness of the metal tube 30 in the distal end region is somewhat reduced, making the metal tube 30 flexible (flexibility), giving the drug solution injection needle 100 excellent ability to follow a blood vessel, and enabling the drug solution injection needle 100 to easily follow the shape of the blood vessel up until the target site.

Note that the slit 33 is a through-slit that extends from the outer circumferential surface of the metal tube to the inner circumferential surface. However, in another example, the slit may be formed not extending through to the inner circumferential surface.

The length (L33 illustrated in FIG. 1) of the slit 33 formed in the distal end region of the base end portion 32 typically ranges from 30 to 400 mm and in a preferable example is 100 mm.

The pitch of the slit 33 is formed so as to become continuously narrower toward the distal end direction. This allows the stiffness of distal end region of the base end portion 32 to be continuously (smoothly) reduced toward the distal end direction. Accordingly, the ease of controlling the drug solution injection needle 100 when guiding it into the target site can be improved. However, the slit formed in the distal end region of the base end portion may be formed having the same pitch.

The insulating layer 40 constituting the drug solution injection needle 100 is a layer made of an electrical insulation material that covers the outer circumferential surface of the base end portion 32 of the metal tube 30.

Since the outer circumferential surface of the base end portion 32 of the metal tube 30 is covered by the insulating layer 40, the distal end portion 31 of the metal tube 30 not covered by the insulating layer 40 can function as an electrode for measuring electric potential and the base end portion 32 of the metal tube 30 can function as the lead of the electrode.

This removes the need for separately providing a ring-shaped electrode on the outer surface of the needle or providing a lead line of the electrode inside or outside the metal tube. This allows the diameter of the drug solution injection needle 100 to be reduced and allows sufficient cavity space to be ensured.

Also, because the insulating layer 40 can close up the slit 33 formed in the distal end region of the base end portion 32 of the metal tube 30, the liquid-tightness of the drug solution injection needle 100 can be ensured.

The length (L31 illustrated in FIG. 2) of the distal end portion 31 of the metal tube 30 that functions as an electrode typically ranges from 0.1 to 4 mm (approximately from 0.007 to 0.3% of the total length of the metal tube 30) and in a preferable example is 0.5 mm.

Note that the insulating layer 40 does not need to cover the outer circumferential surface across the entire length (L100-L10-L20-L31) of the base end portion 32 of the metal tube 30, and in the present embodiment, the region from the distal end of the base end portion 32 extending a certain length is covered by the insulating layer 40.

The length (L40 illustrated in FIG. 1) of the region covered by the insulating layer 40 typically ranges from 60 to 420 mm and in a preferable example is 120 mm.

The insulating layer 40 can be formed by shrinking a heat-shrinkable resin tube in which the base end portion 32 of the metal tube 30 is inserted inside.

Examples of the heat-shrinkable resin tube for forming the insulating layer 40 include polyethylene terephthalate (PET) and polyether block amide copolymer resin (PEBAX (trademark)).

The film thickness of the insulating layer 40 ranges from 10 to 100 μm and in a preferable example is 20 μm.

The drug solution injection needle 100 of the present embodiment together with the gripping portion 50 (the injection port 51 and the connector 53) form the drug solution injection needle device, and a drug solution is injected into the myocardium of a patient using the drug solution injection needle device.

When the drug solution injection needle device is used to inject a drug solution, a syringe containing the drug solution to be supplied to the cavity of the drug solution injection needle 100 is connected to the injection port 51 and the connector 53 is connected to an electrocardiogram device.

The drug solution injection needle 100 of the present embodiment is inserted into a sheath or guiding catheter and in this state is entered into a cavity (cardiac cavity) of a living body. When the distal end of the sheath or guiding catheter reaches at or near the target site specified by mapping, a needle tip of the drug solution injection needle 100 is extended out from the leading end opening to puncture the target site (myocardium).

Figure 4A:
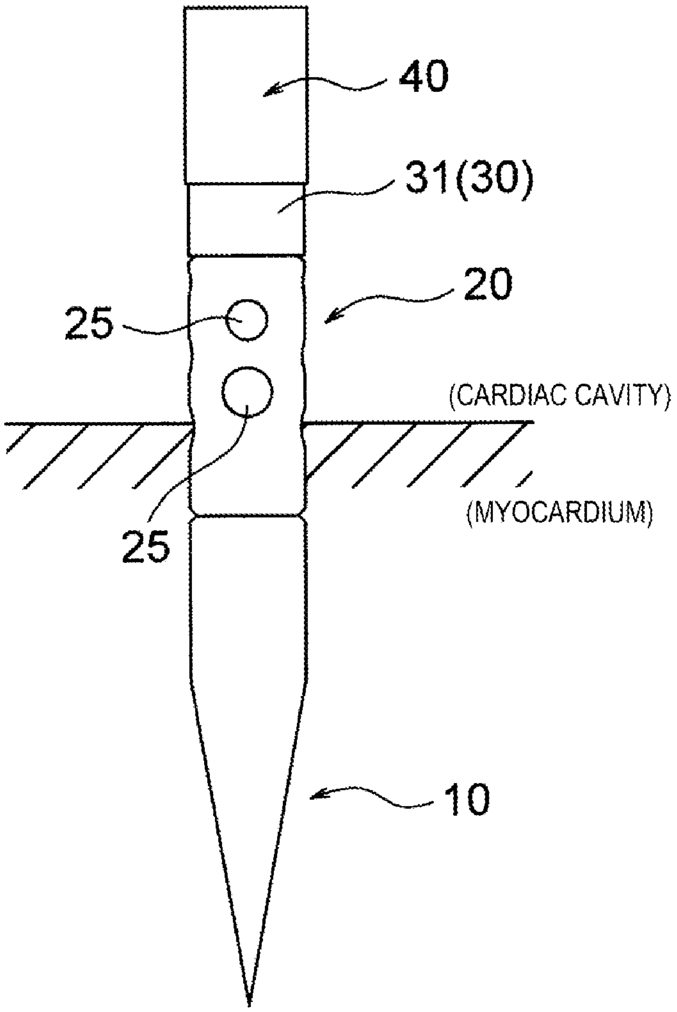
FIG. 4A is an explanatory diagram illustrating a state in which a distal end member and a portion of a connecting tube constituting the drug solution injection needle illustrated in FIG. 1 has been entered inside a heart wall.

FIG. 4A illustrates a state in which the drug solution injection needle 100 has punctured the myocardium and the distal end member 10 and a portion (distal end portion) of the connecting tube 20 have entered inside the heart wall.

At this stage, the remaining portion (base end portion) of the connecting tube 20 including the region where the side holes 25 are formed is located inside the cardiac cavity. Thus, even if an operation is performed to inject the drug solution at this stage, the drug solution would leak out inside the cardiac cavity, meaning that the drug solution cannot be injected in the myocardium.

However, in the state illustrated in FIG. 4A, the electrode (distal end portion 31 of the metal tube 30) located on the base end side of the connecting tube 20 is located inside the cardiac cavity. Thus, there will be no rapid increase (acquisition of electric potential equal to or greater than a certain value) in the electric potential measured by the electrode. Thus, at this stage, the operator does not inject the drug solution.

Figure 4B:
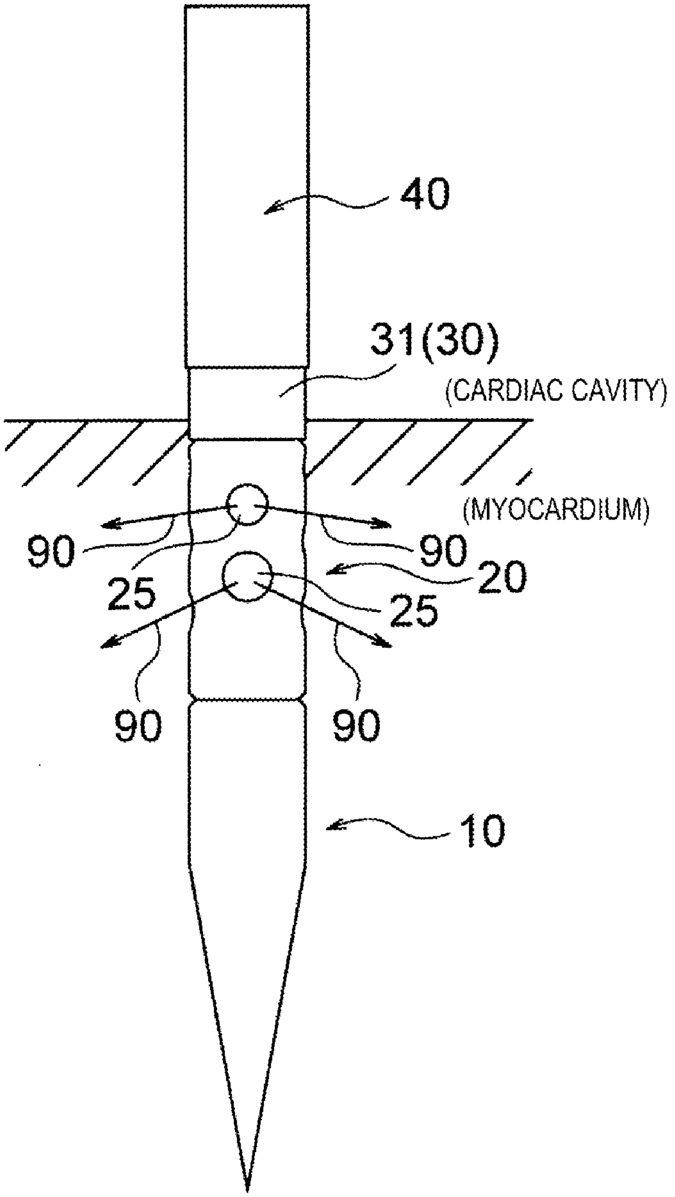
FIG. 4B is an explanatory diagram illustrating a state in which the distal end portion (electrode) of the metal tube constituting the drug solution injection needle illustrated in FIG. 1 has been entered inside a heart wall.

FIG. 4B illustrates a state in which the drug solution injection needle 100 has moved further and the distal end member 10 and the connecting tube 20 are completely embedded inside the heart wall (myocardium), with a portion of the distal end portion 31 (electrode) of the metal tube 30 on the base end side entering inside the heart wall (myocardium).

At this stage, the connecting tube 20 where the side holes 25 are formed is located in the myocardium. Thus, by performing an operation to inject the drug solution at this stage, the drug solution can be injected in the myocardium.

Also, in the state illustrated in FIG. 4B, because the electrode entered in the myocardium is in contact with the myocardial tissue, there is a rapid increase in the electric potential measured by the electrode and an electric potential equal to or greater than a certain value (for example, 2 mV or greater) is acquired. In this manner, the operator injects the drug solution after checking that the electric potential displayed on the monitor of an electrocardiogram device is equal to or greater than a certain value. This allows a drug solution 90 to be reliably injected in the myocardium of a patient from the opening (opening for drug solution injection) of the side holes 25 formed in the connecting tube 20.

An embodiment of the present invention has been described above. However, the drug solution injection needle of the present invention is not limited thereto, and various changes may be made.

For example, a cavity that communicates with the cavity of the connecting tube and the cavity of the metal tube may be formed in the distal end member, and a hole that communicates with the cavity of the distal end member and opens to the outer surface (distal end surface or outer circumferential surface) of the distal end member may be formed. In this case, the side holes may or may not be formed in the outer circumferential surface of the connecting tube.

Figure 5A:
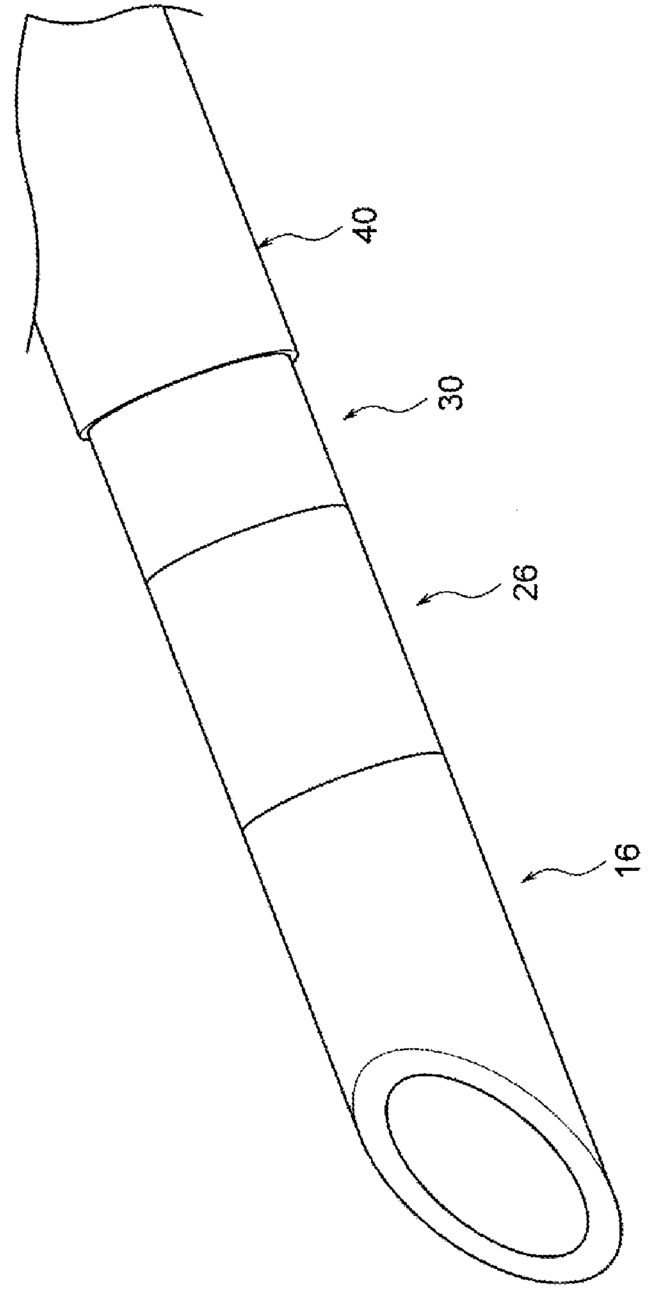
FIG. 5A is a perspective view illustrating a distal end portion of a drug solution injection needle according to a modified example of the present invention.
Figure 5B:
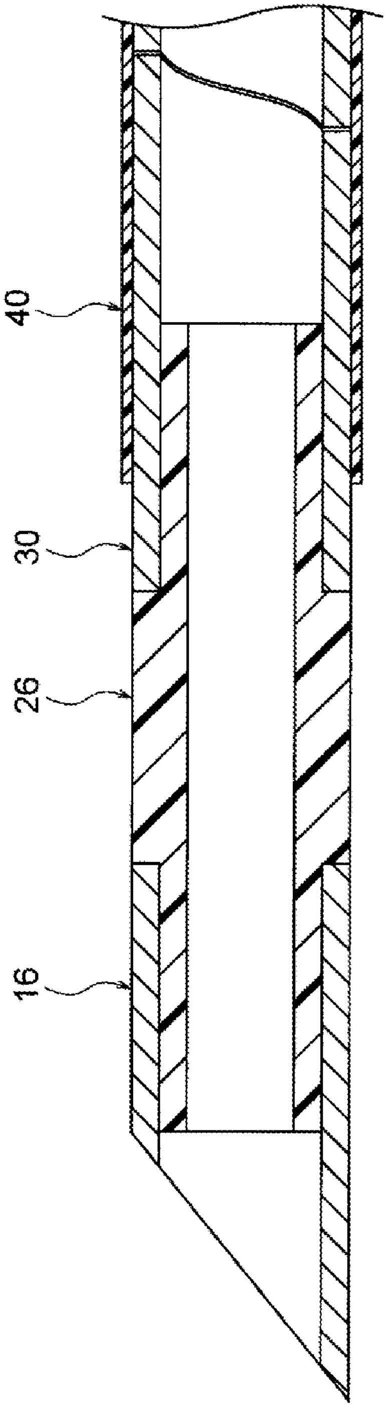
FIG. 5B is a partially enlarged cross-sectional view illustrating the distal end portion of the drug solution injection needle according to the modified example of the present invention.

An example of such a drug solution injection needle is illustrated in FIGS. 5A and 5B. The drug solution injection needle includes a distal end member 16 with only the distal end surface open and a connecting tube 26 with no side holes formed that is connected to the base end side of the distal end member 16.

Drug Solution Injection Needle System

Figure 6:
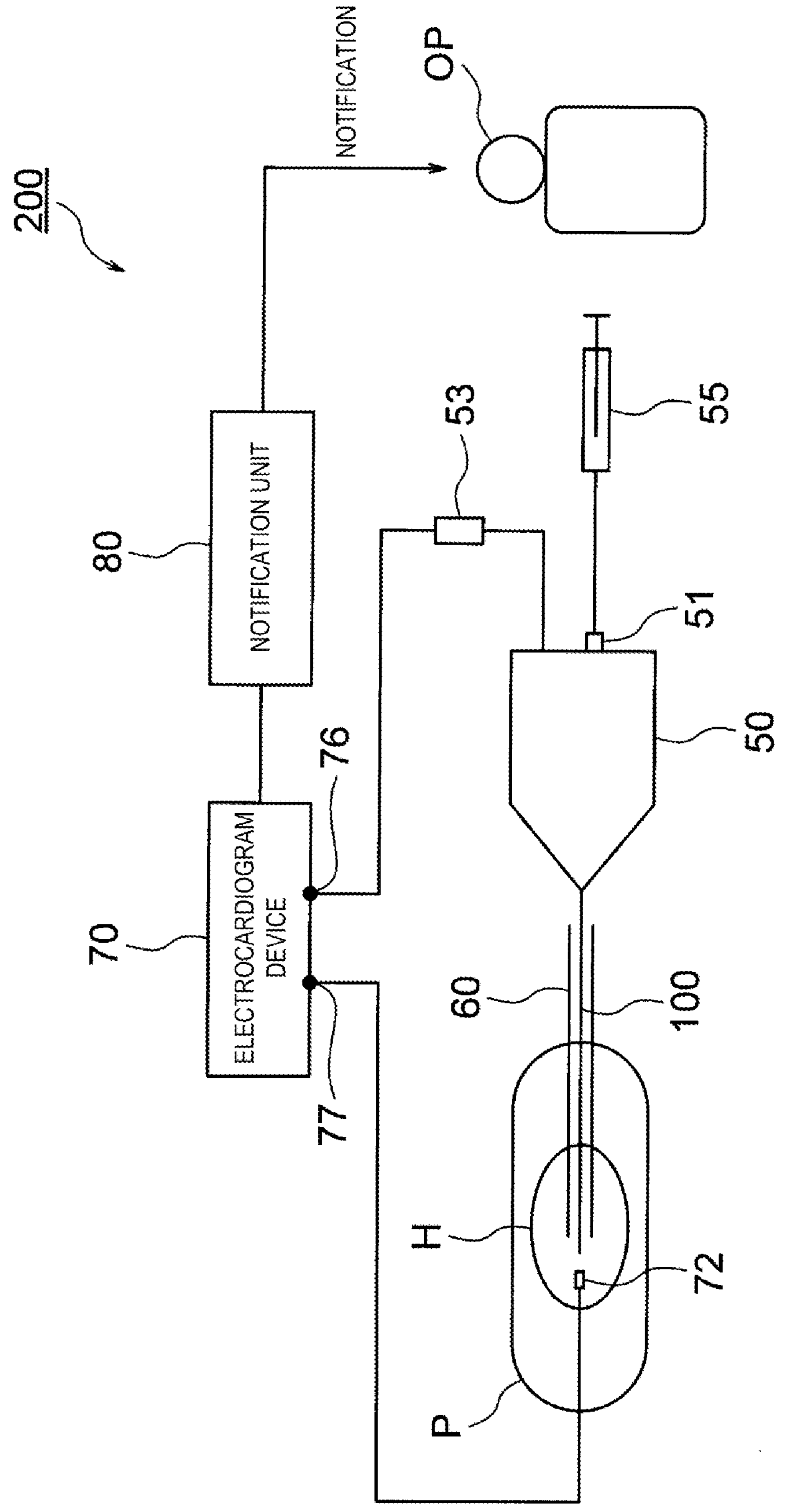
FIG. 6 is an explanatory diagram illustrating a schematic configuration of a drug solution injection needle system according to an embodiment of the present invention.

A drug solution injection needle system 200 of the present embodiment illustrated in FIG. 6 includes the drug solution injection needle 100 of the embodiment described above, the gripping portion 50 installed on the base end side of the metal tube constituting the drug solution injection needle 100, a guiding catheter 60 for guiding the distal end portion of the drug solution injection needle 100 to a cardiac cavity H of a patient P, the injection port 51 for supplying a drug solution to the cavity of the drug solution injection needle 100, the connector 53 electrically connected with the electrode of the drug solution injection needle 100, an electrocardiogram device 70 connected with the connector 53, an indifferent electrode 72 that connects to the electrocardiogram device 70 and is disposed inside (vena cava) the patient P, and a notification unit 80 that notifies an operator OP that the drug solution can be injected when the electric potential measured via the electrode of the drug solution injection needle 100 is equal to or greater than a predetermined value. In the same diagram, 55 denotes a syringe 55 connected to the injection port 51.

As illustrated in FIG. 6, the connector 53 connected to the electrode of the drug solution injection needle 100 is connected to a drug solution injection needle connection connector 76 of the electrocardiogram device 70. Also, the indifferent electrode 72 is connected to an indifferent electrode connection connector 77 of the electrocardiogram device 70.

The indifferent electrode 72 is provided on an electrode catheter (not illustrated) different from the guiding catheter 60 and is disposed in the vena cava of the patient P in a manner that does not pick up the cardiac potential of the patient P.

This makes it possible to measure the electric potential between the electrode of the drug solution injection needle 100 and the indifferent electrode 72 and to sequentially input the measured electric potential information to the electrocardiogram device 70.

The guiding catheter 60 constituting the drug solution injection needle system 200 guides the distal end portion of the drug solution injection needle 100 to the cardiac cavity H of the patient P, with the distal end being first inserted and positioned at or near the target site.

The notification unit 80 constituting the drug solution injection needle system 200 constantly determines whether the electric potential measured via the electrode of the drug solution injection needle 100 is equal to or greater than the predetermined value. When the electric potential is equal to or greater than the predetermined value, the notification unit 80 notifies the operator OP that the drug solution can be injected (the drug solution can be injected in the myocardium).

Here, how the operator OP is notified is not particularly limited and examples include and are not limited to a display of a message on a monitor or the like, a lamp lighting up or blinking, and a buzzer or audio message.

According to the drug solution injection needle system 200 of the present embodiment, by performing an injection operation to supply the drug solution from the syringe 55 into the cavity of the drug solution injection needle 100 after a notification is received from the notification unit 80, the drug solution can be reliably injected to the myocardium of the patient without the need for constantly monitoring via a monitor the electric potential measured by the electrode.

The invention claimed is:

1. A drug solution injection needle that is a hollow needle for puncturing a myocardium of a patient and injecting a drug solution, comprising:

a distal end member, the distal end member being a sharp member and made of metal;

a connecting tube having electrical insulating properties connected to a base end side of the distal end member;

a metal tube connected to a base end side of the connecting tube; and an insulating layer covering an outer circumferential surface of a base end portion of the metal tube, wherein the connecting tube includes a coupling portion connected with the distal end member and at least one hole communicating with a cavity of the connecting tube and open to an outer surface of the connecting tube or the distal end member, and an electrode configured to measure electric potential is formed by a distal end portion of the metal tube not covered by the insulating layer, wherein the distal end member is disconnected with the cavity of the connecting tube by the coupling portion of the connecting tube.

2. The drug solution injection needle according to claim 1, wherein a distal end of the distal end member is closed, and the at least one hole includes a plurality of side holes communicating with the cavity of the drug solution injection needle and open to the outer circumferential surface of the connecting tube.

3. The drug solution injection needle according to claim 2, wherein side hole groups including the plurality of side holes arranged in an axial direction of the connecting tube are disposed at even angular intervals apart in a circumferential direction of the connecting tube.

4. The drug solution injection needle according to claim 3, wherein the side holes of the side hole groups located on a distal end side have a lager diameter than side holes located on the base end side.

5. The drug solution injection needle according to claim 1, wherein a helical slit is formed in a distal end region of the base end portion of the metal tube.

6. The drug solution injection needle according to claim 1, wherein the drug solution is a cardiac regenerative cell formulation.

7. A drug solution injection needle system, comprising:

the drug solution injection needle according to claim 1; and a notification unit configured to notify an operator that injection of the drug solution is possible when an electric potential measured by the electrode of the drug solution injection needle is equal to or greater than a predetermined value.

* * * * *